(12) United States Patent
Holma et al.

(10) Patent No.: US 9,374,750 B2
(45) Date of Patent: Jun. 21, 2016

(54) METHOD AND APPARATUS FOR HANDOVER MANAGEMENT

(75) Inventors: Harri Kalevi Holma, Helsinki (FI); Hannu Pekka Matias Vaitovirta, Espoo (FI); Antti Anton Toskala, Espoo (FI)

(73) Assignee: Nokia Siemens Networks Oy, Espoo (FI)

( * ) Notice: Subject to any disclaimer, the term of this patent is extended or adjusted under 35 U.S.C. 154(b) by 0 days.

(21) Appl. No.: 14/111,203

(22) PCT Filed: Apr. 11, 2011

(86) PCT No.: PCT/EP2011/055611
§ 371 (c)(1),
(2), (4) Date: Oct. 11, 2013

(87) PCT Pub. No.: WO2012/139626
PCT Pub. Date: Oct. 18, 2012

(65) Prior Publication Data
US 2014/0031043 A1    Jan. 30, 2014

(51) Int. Cl.
*H04W 74/08* (2009.01)
*H04W 72/04* (2009.01)
*H04W 72/10* (2009.01)
*H04W 36/08* (2009.01)
*H04W 72/12* (2009.01)

(52) U.S. Cl.
CPC .......... *H04W 36/08* (2013.01); *H04W 72/1289* (2013.01)

(58) Field of Classification Search
CPC .............. H04W 72/04; H04W 74/002; H04W 74/0833; H04W 84/047; H04W 36/0072; H04W 72/042; H04W 36/08; H04W 36/0033; H04W 36/0083; H04W 36/30; H04W 36/0005; H04W 36/0011; H04W 36/0055; H04W 36/0061; H04W 36/06; H04W 36/245; H04W 36/36; H04W 72/00; H04W 72/0406
USPC ................ 455/450, 436–440, 446, 420, 423, 455/456.1, 507, 68; 370/310.2, 329, 331, 370/332, 350, 414, 438, 252, 241, 330, 236, 370/311, 316, 328, 392, 404.2, 418, 436, 370/446, 420, 423, 440, 456.1, 507, 68
See application file for complete search history.

(56) References Cited

U.S. PATENT DOCUMENTS

| 6,108,322 A | 8/2000 | Kotzin et al. ................. 370/333 |
| 2008/0267131 A1* | 10/2008 | Kangude et al. .............. 370/331 |

(Continued)

FOREIGN PATENT DOCUMENTS

| CN | 1177266 A | 3/1998 |
| CN | 1278397 A | 12/2000 |

(Continued)

OTHER PUBLICATIONS

3GPP Standard; 3GPP TS 36.300, 3rd Generation Partnership Project (3GPP), Mobile Competence Centre ; 650, Route des Lucioles ; F-06921 Sophia-Antipolis Cedex ; France, No. V10.3.0, Apr. 5, 2011, pp. 1-197, XP050477t 75, [retrieved Apr. 5, 2011].*

(Continued)

*Primary Examiner* — Inder Mehra
(74) *Attorney, Agent, or Firm* — Harrington & Smith (57) ABSTRACT

A method includes receiving information indicating a user equipment is to be handed over from a source base station and scheduling transmission of a control channel for said user equipment in dependence on identity information associated with said user equipment.

6 Claims, 4 Drawing Sheets

(56) References Cited

U.S. PATENT DOCUMENTS

2010/0304748 A1   12/2010   Henttonen et al. ............ 455/436
2011/0014922 A1*   1/2011   Jen ...................... H04W 74/002
                                                                    455/450

FOREIGN PATENT DOCUMENTS

| CN | WO-01/15482 A1 | 3/2001 | |
| CN | 1382360 A | 11/2002 | |
| CN | 101010980 A | 8/2007 | |
| CN | 101064943 A | 10/2007 | |
| WO | WO-99/22546 A1 | 5/1999 | |
| WO | WO-2006/005028 A1 | 1/2006 | |
| WO | WO 2010/129606 A1 * | 11/2010 | ................ H04L 5/00 |
| WO | WO 2010/150662 A1 | 12/2010 | |

OTHER PUBLICATIONS

3GPP TSG RAN WG1 Meeting #51bis, Sevilla, Spain, Jan. 14-18, 2008, R1-080028, "Configuration of PDCCH Monitoring Set", Samsung, 3 pgs.

3GPP TSG RAN1 #52bis, Shenzhen, China, Mar. 31-Apr. 4, 2008, R1-081672, "PDCCH Search Space Assignment Hashing Function", Motorola, 7 pgs.

3GPP TSG RAN WG1 Meeting #60bis, Beijing, China, Apr. 12-16, 2010, R1-101982, "LTE non-CA based HetNet Support", Huawei, 7 pgs.

3GPP TSG RAN WG1 #61, Montreal, Canada, May 10-14, 2010, R1-102831, "Rel-8/9 compatible PDCCH interference mitigation schemes for Het-Nets", Texas Instruments, 8 pgs.

3GPP TSG RAN WG1 #61 bis, Jun. 28-Jul. 2, 2010, Dresden, Germany, R1-103713, "Views on PDCCH Interference Mitigation for HET-Nets", Texas Instruments, 11 pgs.

Joint 3GPP TSG RAN WG2/RAN WG3, Cannes, France, UK, Oct. 10-14, 2005, R3-055130, "Discussion on Intra-access mobility in LTE_Active", Lucent Technologies, 3 pgs.

3GPP TS 36.300 V10.3.0 (Mar. 2011), "$3^{rd}$ Generation Partnership Project; Technical Specification Group Radio Access Network; Evolved Universal Terrestrial Radio Access (E-UTRA) and Evolved Universal Terrestrial Radio Access Network (E-UTRAN); Overall description; Stage 2 (Release 10)", 197 pgs.

* cited by examiner

METHOD AND APPARATUS FOR HANDOVER MANAGEMENT

The invention relates a method and apparatus and in particular but not exclusively to a method and apparatus and in particular but not exclusively to a method and apparatus for use in handover.

A communication system can be seen as a facility that enables communication sessions between two or more entities such as fixed or mobile communication devices, base stations, servers and/or other communication nodes. A communication system and compatible communicating entities typically operate in accordance with a given standard or specification which sets out what the various entities associated with the system are permitted to do and how that should be achieved. For example, the standards, specifications and related protocols can define the manner how communication devices can access the communication system and how various aspects of communication shall be implemented between communicating devices. A communication can be carried on wired or wireless carriers. In a wireless communication system at least a part of the communication between at least two stations occurs over a wireless link.

Examples of wireless systems include public land mobile networks (PLMN) such as cellular networks, satellite based communication systems and different wireless local networks, for example wireless local area networks (WLAN). A wireless system can be divided into cells, and hence these are often referred to as cellular systems. A cell is provided by a base station. Cells can have different shapes and sizes. A cell can also be divided into sectors. Regardless of the shape and size of the cell providing access for a user equipment, and whether the access is provided via a sector of a cell or a cell, such area can be called radio service area or access area. Neighbouring radio service areas typically overlap, and thus a communication in an area can listen to more than one base station.

A user can access the communication system by means of an appropriate communication device. A communication device of a user is often referred to as user equipment (UE) or terminal. A communication device is provided with an appropriate signal receiving and transmitting arrangement for enabling communications with other parties. Typically a communication device is used for enabling receiving and transmission of communications such as speech and data. In wireless systems a communication device provides a transceiver station that can communicate with another communication device such as e.g. a base station of an access network and/or another user equipment. The communication device may access a carrier provided by a station, for example a base station, and transmit and/or receive communications on the carrier.

An example of communication systems attempting to satisfy the increased demands for capacity is an architecture that is being standardized by the 3rd Generation Partnership Project (3GPP). This system is often referred to as the long-term evolution (LTE) of the Universal Mobile Telecommunications System (UMTS) radio-access technology. The LTE aims to achieve various improvements, for example reduced latency, higher user data rates, improved system capacity and coverage, reduced cost for the operator and so on. A further development of the LTE is often referred to as LTE-Advanced. The various development stages of the 3GPP LTE specifications are referred to as releases.

In LTE-Advanced the network nodes can be wide area network nodes such as a macro eNodeB B (eNB) which may, for example, provide coverage for an entire cell. A user equipment which is associated with a source cell may be handed over to a target cell.

According to an aspect, there is method comprising: receiving information indicating a user equipment is to be handed over from a source base station; and scheduling transmission of a control channel for said user equipment in dependence on identity information associated with said user equipment.

The identity information may comprises at least one of user equipment identity and cell identity The control channel may comprise a control channel to be transmitted by a target base station.

The control channel may comprise a physical downlink control channel.

The scheduling may further comprise scheduling said control channel from the target base station for said user equipment at a time when a corresponding control channel from a source base station is not transmitted.

The source base station and target base station may comprise synchronised based stations.

The information indicating a user equipment is to be handed over from a source base station may comprise a handover message.

The method may comprise receiving said handover message from at least one of the source base station and said user equipment.

The handover message may comprise a handover command.

The method may comprise transmitting said control channel to said user equipment prior to said receiving of said handover message.

The information indicating a user equipment is to be handed over may be provided by signals received by said target base station from said user equipment.

The method may comprise determining strength of said received signals, said received signal strength indicating that the user equipment is to be handed over.

The method may be performed in said target base station.

According to another aspect, there is provided a method comprising; providing information indicating a user equipment is to be handed over to a target base station; and monitoring a control channel at time periods in dependence on identity information associated with said user equipment.

The identity information may comprise at least one of user equipment identity and cell identity The control channel may comprise a control channel transmitted by said target base station.

The control channel may comprise a physical downlink control channel.

The information may be provided to at least one of a source base station and a target base station.

The information may comprise measurement information.

The method may comprise monitoring said control channel prior to providing said information.

The method may comprise additionally monitoring a control channel of a source base station.

The method may be performed by a user equipment.

According to another aspect, there is provided apparatus comprising; means for receiving information indicating a user equipment is to be handed over from a source base station; and means for scheduling transmission of a control channel for said user equipment in dependence on identity information associated with said user equipment.

The identity information may comprise at least one of user equipment identity and cell identity The control channel may comprise a control channel to be transmitted by a target base station.

The control channel may comprise a physical downlink control channel.

The means for scheduling may be configured to schedule said control channel from the target base station for said user equipment at a time when a corresponding control channel from a source base station is not transmitted.

The source base station and target base station may comprise synchronised based stations.

The information indicating user equipment is to be handed over from a source base station may comprise a handover message.

The receiving means may be configured to receive said handover message from at least one of the source base station and said user equipment.

The handover message may comprise a handover command.

The apparatus may comprise means for transmitting said control channel to said user equipment prior to receiving of said handover message.

The information indicating a user equipment is to be handed over may be provided by signals received by said receiving means from said user equipment.

The apparatus may comprise means for determining strength of said received signals, said received signal strength indicating that the user equipment is to be handed over.

A base station may comprise the apparatus.

According to an aspect, there is provided an apparatus comprising: means for providing information indicating a user equipment is to be handed over to a target base station; and means for monitoring a control channel at time periods in dependence on identity information associated with said user equipment.

The identity information may comprise at least one of user equipment identity and cell identity The control channel may comprise a control channel transmitted by said target base station.

The control channel may comprise a physical downlink control channel.

The information may be provided to at least one of a source base station and a target base station.

The information may comprise measurement information.

The monitoring means may be configured to monitor said control channel prior to providing said information.

The monitoring means may be configured to additionally monitor a control channel of a source base station.

A user equipment may comprise the apparatus.

According to another aspect, there is provided an apparatus comprising at least one processor and at least one memory including computer program code, the at least one memory and computer program code configured, with the at least one processor, to cause the apparatus to: provide information indicating a user equipment is to be handed over to a target base station; and monitor a control channel at time periods in dependence on identity information associated with said user equipment.

According to another aspect, there is provided an apparatus comprising at least one processor and at least one memory including computer program code, the at least one memory and computer program code configured, with the at least one processor, to cause the apparatus to: receive information indicating a user equipment is to be handed over from a source base station; and schedule transmission of a control channel for said user equipment in dependence on identity information associated with said user equipment.

According to another aspect, there is provided a method comprising: receiving at a user equipment a control channel from a source base station; and causing said user equipment to change to receiving a corresponding control channel from a targeted base station.

According to another aspect, there is provided apparatus comprising: means for receiving at a user equipment a control channel from a source base station; and means for causing said user equipment to change to receiving a corresponding control channel from a targeted base station According to another aspect, there is provided a method comprising: receiving a handover request for a user equipment, and scheduling a control channel from a target base station for said use equipment at a time when said corresponding control channel from said source base station is not transmitted.

According to another aspect, there is provided apparatus comprising: means for receiving a handover request for a user equipment, and means for scheduling a control channel from a target base station for said use equipment at a time when said corresponding control channel from said source base station is not transmitted.

According to another aspect, there is provided a method comprising: receiving a handover request for a user equipment; and scheduling transmission of a control channel for said user equipment using a limited set of control channel configurations at defined times.

According to another aspect, there is provided apparatus comprising: means for receiving a handover request for a user equipment; and means for scheduling transmission of a control channel for said user equipment using a limited set of control channel configurations at defined times It should be appreciated that any feature of any aspect may be combined with any other feature of any other aspect.

Embodiments will now be described in further detail, by way of example only, with reference to the following examples and accompanying drawings, in which.

In the following certain exemplifying embodiments are explained with reference to a wireless or mobile communication system serving mobile communication devices. Before explaining in detail the exemplifying embodiments, certain general principles of a wireless communication system, access systems thereof, and mobile communication devices are briefly explained with reference to FIGS. 1 to 3 to assist in understanding the technology underlying the described examples.

Figure 1:
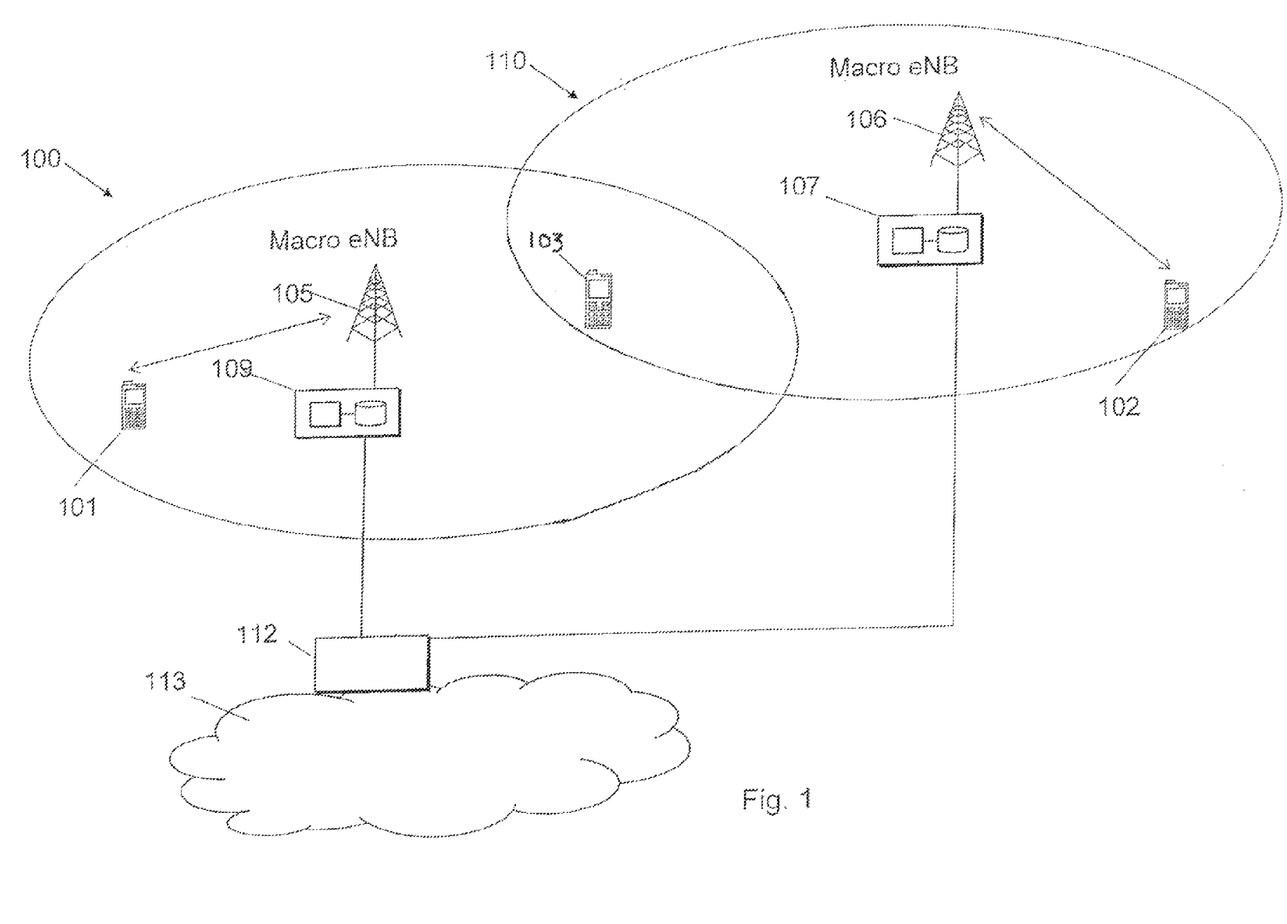
FIG. 1 shows a schematic diagram of a network according to some embodiments.

A communication device or user equipment 101, 102, 103, is typically provided wireless access via at least one base station or similar wireless transmitter and/or receiver node of an access system. In FIG. 1 two neighbouring and overlapping access systems or radio service areas 100, 110 are shown being provided by base stations 105, 106.

However, it is noted that instead of two access systems, any number of access systems can be provided in a communication system. An access system can be provided by a cell of a cellular system or another system enabling a communication device to access a communication system. A base station site 105, 106 can provide one or more cells. A base station can also provide a plurality of sectors, for example three radio sectors, each sector providing a cell or a subarea of a cell. All sectors within a cell can be served by the same base station. A radio link within a sector can be identified by a single logical identification belonging to that sector. Thus a base station can provide one or more radio service areas. Each communication device 101, 102, 103, and base station 105, 106 may have one or more radio channels open at the same time and may send signals to and/or receive signals from more than one source.

Figure 3:
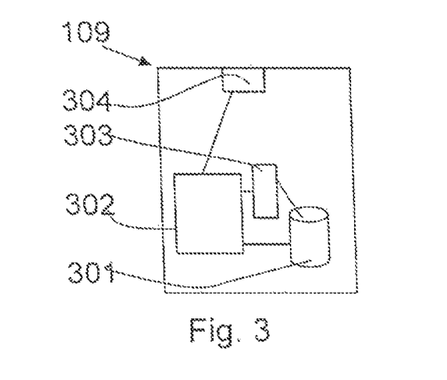
FIG. 3 shows a schematic diagram of a control apparatus according to some embodiments.

Base stations 105, 106, are typically controlled by at least one appropriate controller apparatus 109, 107 so as to enable operation thereof and management of mobile communication devices 101, 102, 103, in communication with the base stations 105, 106, 108. The control apparatus 107, 109 can be interconnected with other control entities. The control apparatus 107, 109 can typically be provided with memory capacity 301 and at least one data processor 302. The control apparatus 107, 109 and functions may be distributed between a plurality of control units. In some embodiments, each base station 105, 106 can comprise a control apparatus 109, 107. In alternative embodiments, two or more base stations may share a control apparatus. Currently LTE does not have a separate radio network controller. In some embodiments the control apparatus may be respectively provided in each base station.

The cell borders or edges are schematically shown for illustration purposes only in FIG. 1. It shall be understood that the sizes and shapes of the cells or other radio service areas may vary considerably from the similarly sized omni-directional shapes of FIG. 1.

In particular, FIG. 1 depicts two wide area base stations 105, 106, which can be macro-eNBs 105, 106. The macro-eNBs 105, 106 transmit and receive data over the entire coverage of the cells 100 and 110 respectively. Alternatively, in LTE-Advanced, network nodes can be small area network nodes such as Home eNBs (HeNB) (femto cells) or pico eNodeBs (pico-eNB). HeNBs may be configured to support local offload and may support any UE or UEs belonging to a closed subscriber group (CSG) or an open subscriber group (OSG). In some instances a combination of wide area network nodes and small area network nodes can be deployed using the same frequency carriers (e.g. co-channel deployment). The coverage of the smaller area base station is generally smaller than the coverage of the wide area base stations 105, 106. The coverage provided by smaller area nodes (pico or femto nodes) may overlap with the coverage provided by the macro-eNBs. Pico eNBs can be used to extend coverage of the macro-eNBs outside the original cell coverage of the macro-eNBs. The pico eNB can also be used to provide cell coverage in "gaps" or "shadows" where there is no coverage within the existing cells and/or may serve "hot spots". In some embodiments, the smaller area node can be a femto or Home eNB which can provide coverage for a relatively small area such as the home. Some environments may have both pico and femto cells.

As shown, the radio service areas can overlap. Thus signals transmitted in an area can interfere with communications in another area.

The communication devices 101, 102, 103, can access the communication system based on various access techniques, such as code division multiple access (CDMA), or wideband CDMA (WCDMA). Other examples include time division multiple access (TDMA), frequency division multiple access (FDMA) and various schemes thereof such as the interleaved frequency division multiple access (IFDMA), single carrier frequency division multiple access (SC-FDMA) and orthogonal frequency division multiple access (OFDMA), space division multiple access (SDMA) and so on.

Some non-limiting examples of the recent developments in communication systems are the long-term evolution (LTE) of the Universal Mobile Telecommunications System (UMTS) that is being standardized by the 3rd Generation Partnership Project (3GPP). As explained above, further development of the LTE is referred to as LTE-Advanced. Non-limiting examples of appropriate access nodes are a base station of a cellular system, for example what is known as NodeB (NB) in the vocabulary of the 3GPP specifications. The LTE employs a mobile architecture known as the Evolved Universal Terrestrial Radio Access Network (E-UTRAN). Base stations of such systems are known as evolved Node Bs (eNBs) and may provide E-UTRAN features such as user plane Radio Link Control/Medium Access Control/Physical layer protocol (RLC/MAC/PHY) and control plane Radio Resource Control (RRC) protocol terminations towards the user devices. Other examples of radio access system include those provided by base stations of systems that are based on technologies such as wireless local area network (WLAN) and/or WiMax (Worldwide Interoperability for Microwave Access).

In FIG. 1 the base stations 105, 106, of the access systems can be connected to a wider communications network 113. The controller apparatus 107, 109 may be provided for coordinating the operation of the access systems. A gateway function 112 may also be provided to connect to another network via the network 113. The smaller base station 108 can also be connected to the other network by a separate gateway function 111. The base stations 105, 106, can be connected to each other by a communication link for sending and receiving data. The communication link can be any suitable means for sending and receiving data between the base stations 105, 106 and in some embodiments the communication link is an X2 link.

The other network may be any appropriate network. A wider communication system may thus be provided by one or more interconnect networks and the elements thereof, and one or more gateways may be provided for interconnecting various networks.

Figure 2:
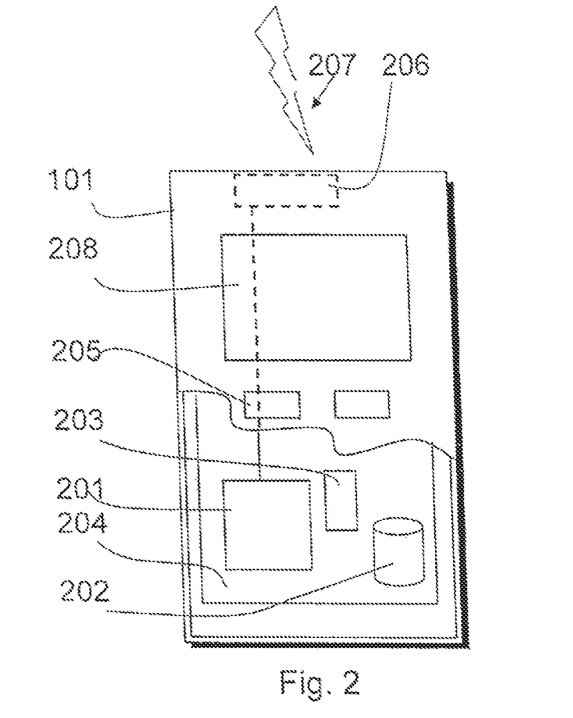
FIG. 2 shows a schematic diagram of a mobile communication device according to some embodiments.

The communication devices will now be described in more detail with reference to FIG. 2. FIG. 2 shows a schematic, partially sectioned view of a communication device 101 that a user can use for communication. Such a communication device is often referred to as user equipment (UE) or terminal. An appropriate communication device may be provided by any device capable of sending and receiving radio signals. The communication device may be mobile. Non-limiting examples of a communication device include a mobile station (MS) such as a mobile phone or what is known as a 'smart phone', a portable computer provided with a wireless interface card or other wireless interface facility, personal data assistant (PDA) provided with wireless communication capabilities, or any combinations of these or the like. A communication device may provide, for example, communication of data for carrying communications such as voice, electronic mail (email), text message, multimedia and so on. Users may thus be offered and provided numerous services via their communication devices. Non-limiting examples of these services include two-way or multi-way calls, data communication or multimedia services or simply an access to a data communications network system, such as the Internet. Users may also be provided broadcast or multicast data. Non-limiting examples of the content include downloads, television and radio programs, videos, advertisements, various alerts and other information.

The communication device 101 may receive signals over an air interface 207 via appropriate apparatus for receiving and may transmit signals via appropriate apparatus for transmitting radio signals. In FIG. 2 transceiver apparatus is designated schematically by block 206. The transceiver apparatus 206 may be provided for example by means of a radio part and associated antenna arrangement. The antenna arrangement may be arranged internally or externally to the mobile device.

A mobile device is also typically provided with at least one data processing entity 201, at least one memory 202 and other possible components 203 for use in software and hardware aided execution of tasks it is designed to perform, including control of access to and communications with access systems and other communication devices. The data processing, storage and other relevant control apparatus can be provided on an appropriate circuit board and/or in chipsets. This feature is denoted by reference 204.

The user may control the operation of the mobile device by means of a suitable user interface such as key pad 205, voice commands, touch sensitive screen or pad, combinations thereof or the like. A display 208, a speaker and a microphone can be also provided. Furthermore, a mobile communication device may comprise appropriate connectors (either wired or wireless) to other devices and/or for connecting external accessories, for example hands-free equipment, thereto.

FIG. 3 shows an example of a control apparatus 109 (or 107) for a communication system, for example to be coupled to, included in and/or for controlling a station of an access system. In some embodiments the base stations 105, 106, each comprise a separate control apparatus, such as shown in FIG. 3. The control apparatus 109 can be arranged to provide control of communications by communication devices that are in the service area of the system. The control apparatus 109 can be configured to provide control functions in association with generation and communication of transmission patterns and other related information and for muting signals by means of the data processing facility in accordance with certain embodiments described below. For this purpose the control apparatus 109 comprises at least one memory 301, at least one data processing unit 302, 303 and an input/output interface 304. Via the interface the control apparatus can be coupled to a receiver and a transmitter of the base station. The control apparatus 109 can be configured to execute an appropriate software code to provide the control functions.

The LTE system currently has frequency reuse where neighbouring cells use the same frequency. Therefore, the inter-cell interference may be high at the cell edge and this may limit the available data rates. Currently LTE radio uses transmission and reception from one cell at a time. Currently no soft handover has been defined for LTE. Another issue for cell edge performance is handover delay and/or hysteresis. Typical handover latency may be more than 1 second due to measurement averaging. The handover hysteresis maybe typically 4 dB, which means that the target cell must be 4 dB better than the current cell before handover is executed. Therefore, UE may not always be connected to the best cell at the cell edge conditions. Cell edge performance may be affected by one or more of the following:

frequency reuse may make inter-cell interference high; handover delay may cause the UE to be connected to the non-optimal cell; and handover hysteresis may cause the UE to be connected to a non-optimal cell.

The issues may, if combined with high speed mobility, cause call drops. The connection may get dropped after UE has sent a measurement report but before UE has received the reconfiguration command from old eNodeB.

Soft handover is used in WCDMA and HSUPA, but is not currently proposed with LTE. Site selection transmit diversity was defined in 3GPP Release 99 but not implemented and removed in Release 5. Coordinated multipoint transmission (CoMP) has been studied in Release 10 and 11. This assumed very high capacity and low delay transport connection. Enhanced serving cell change has been proposed in HSDPA. These methods in WCDMA may be built under the assumption that the connection exists for a cell (part of the active set) and the data path is directed from one of the existing base stations in the active set which has become the best. In current LTE proposals however a UE is only receiving data and connected to a single base station and the handover is hard handover. It should be noted that CoMP is where a UE is preconfigured from which eNodeBs the UE is expected to receive data, similar to soft handover.

Figure 4:
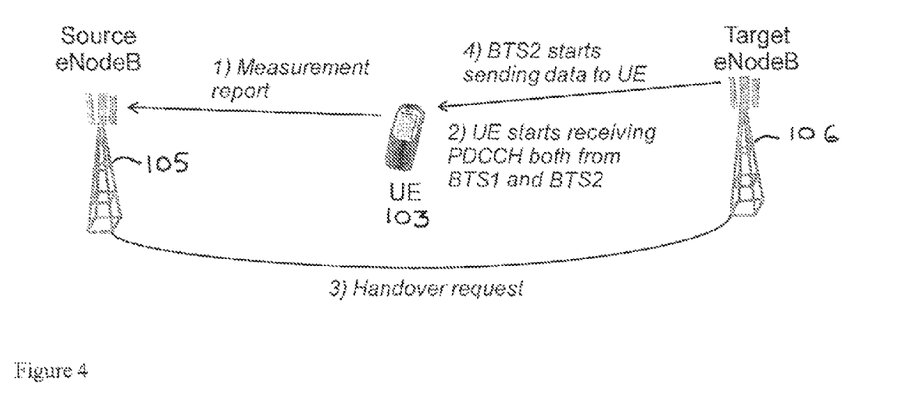
FIG. 4 shows schematically a source eNB, a target eNB and a UE.
Figure 5:
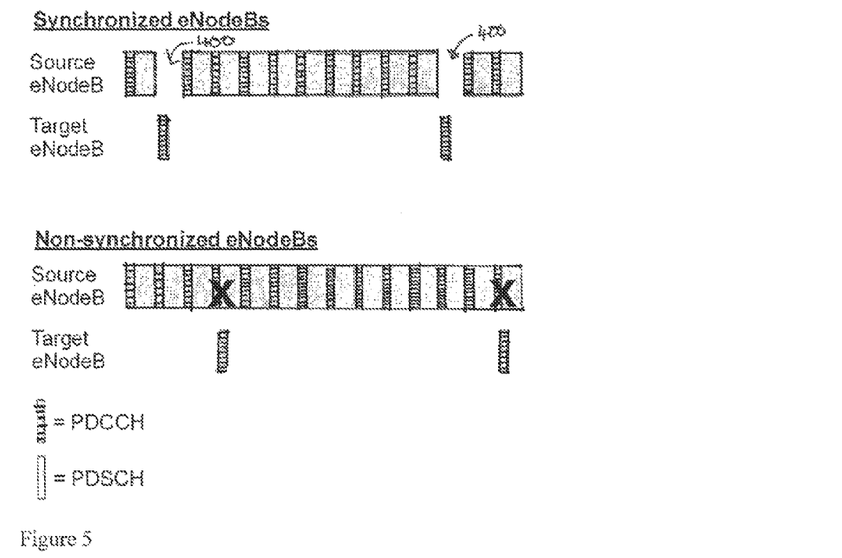
FIG. 5 shows channels of the source and target eNBs in a synchronised scenario and a non synchronised scenario.

Reference is now made to FIGS. 4 and 5 which show some embodiments of the invention. In FIG. 4, the two base stations 105 and 106 are shown with the user equipment 103. In the example shown, the user equipment 103 is associated with the source eNB 105. The target eNB 106 is the base station to which the user equipment is to be handed over. Referring back to FIG. 1, it can be seen that the user equipment 103 is in an area of overlap of the two cells of the source eNB 105 and the target eNB 106.

It should be appreciated that handover may be between two macro cells, a macro cell and a pico cell, a macro cell and a femto cell, two pico cells, a pico cell and a femto cell or two femto cells. In some embodiments, handover may occur more frequently with smaller cells. Corner effects, particularly with smaller cells may change the path loss rapidly when a UE for example drives behind a building.

As referenced 1) in FIG. 4, the user equipment 103 sends a measurement report to the source eNB 105. The measurement report will contain information about measurements made by the user equipment. In particular, the measurement report may include information about the strength of signals received at the user equipment from either the source eNB or the target eNodeB or both. A user equipment will typically make one or more measurements of one or more parameters. One or more of those measurements of one or more parameters may be used in embodiments.

Additionally or alternatively, the UE equipment may send information indicating that the UE should be handed over to the target eNB or information from which the source eNB is able to determine that handover is required.

After the measurement report has been sent to the source eNB, the user equipment may start to receive the PDCCH (physical downlink control channel) from the target eNB. In one embodiment, the user equipment will start monitoring for the PDCCH from the target eNB if the user equipment determines that the user equipment should be handed over to the target eNB. This may, for example, be based on an analysis by the user equipment of the measurement information and/or may be dependent on information received from the source eNB. In one alternative, the user equipment may monitor for the PDCCH from the target eNB periodically.

In another embodiment the UE has a separate threshold level from the one used for sending measurement reports, to be used for considering another cell as a target cell and initiating decoding of the PDCCH of the source cell. The PDCCH in such a case may occur at predefined time instants and/or with limited configurations in order to limit the needed blind decodes and other processing needed for extra decoding.

It should be appreciated that the user equipment may receive the PDCCH from both the source eNB and the target eNB, referenced 2). This will be explained in more detail below with reference to FIG. 5. The eNodeB sends via the PDCCH (physical downlink control channel) information about the resource allocation to the UE. The eNodeB will then send the PDSCH (physical downlink shared channel) to the corresponding UE.

In some embodiments, the user equipment does not need to listen to the target eNB 106 continuously. Rather, the user equipment monitors the PDCCH periodically.

In one embodiment, once the source eNB 105 has received the measurement report from the user equipment and the source eNB determines that the user equipment is to be handed over to the target eNB, the source eNB will send the handover request referenced 3), in FIG. 4 to the target eNB 106. In one embodiment, the source eNB decides that the user equipment is to be handed over based on the information in the measurement report. In an alternative embodiment, the measurement report includes information indicating that the user equipment is to be handed over from the source eNB. Thus, in this latter embodiment, the user equipment makes an initial handover decision. In one further alternative, the decision as to whether to handover the user equipment is made in combination by the user equipment and the source eNB.

It should be appreciated that the source eNB and target eNB can communicate in any suitable manner. For example, the source eNB and target eNB may have a connection there between, the so-called X2 connection.

In one embodiment, the user equipment may start monitoring the target eNB as soon as the measurement report has been sent to the source eNB. The UE may start monitoring the PDCCH from the target cell immediately after having detected that the UE needs to send the measurement report or indication that the new cell has become stronger than the current cell. The UE may be listening to the target cell PDCCH even before the UE sends the measurement report or information. From UE point of view, the target cell may be considered to be the cell that is strongest and may monitor the PDCCH of the target cell.

In one embodiment, the user equipment may delay listening to the target eNB. This, for example, may be to allow sufficient time for the source eNB to send the handover request to the target eNB. For example the delay between the UE providing the measurement report and the target eNB 106 transmitting the PDDCH to the UE may be around 50 ms. The UE may delay monitoring the PDDCH of the target eNB to take into account this delay.

In one embodiment, the source eNB delivers the handover request to the target eNB and the target eNB starts transmitting the PDCCH to the user equipment. The handover request may include identity information relating the UE and/or the cell ID. In one alternative embodiment, there may be an exchange of two or more messages between the source eNB 105 and the target eNB 106 before the target eNB starts transmitting the PDCCH to the user equipment.

In one embodiment, the possible transmission times on the PDCCH from the target eNB to the user equipment are predefined. For example, in one embodiment, the transmission times are predefined based on at least one of the user equipment identity and cell identity. This means that the UE will know when to monitor the PDDCH of the target eNB. The cell identity may be the cell ID of the source cell or the target cell. The UE ID and/or the cell ID may be provided in the handover request from the source eNB. In other embodiments, other methods may be used to ensure that the UE monitors the PDCCH of the target eNB at the time when that PDCCH contains information for that eNB. For example, the source eNB may select a time and provide that information to both the target eNB and the UE.

However, it should be appreciated that in other embodiments, other methods may be used to ensure that the user equipment knows when it needs to check the PDCCH from the target eNB. The PDCCH may provide channel allocation information for the UE.

If the source eNB and target eNB are synchronised, the source eNB will not transmit on the PDCCH to the user equipment that the target eNB transmits to the UE on the PDCCH. If the eNBs are not synchronised, the user equipment will skip reception of the overlapping PDCCH channel from the source eNB, when the UE receives the PDDCH from the target eNB. This will be discussed in more detail with reference to FIG. 5.

In one embodiment, the user equipment receives a reconfiguration message from the source eNB and the user equipment proceeds with handover. When the handover has been completed, the user equipment will send a reconfiguration complete message to the target eNB. In alternative embodiment, the user equipment may receive information from the target eNB on the PDCCH and will send a reconfiguration complete message to the target eNB.

Once the handover has been completed, the target eNB will send data to the user equipment, as referenced 4) in FIG. 4.

In one embodiment the UE may be advised in a message if the target and/or source base station support embodiments. This message can be any suitable message and may for example be a measurement configuration message. This may allow backwards compatibility of the some embodiments with existing systems.

Reference is now made to FIG. 5. FIG. 5 shows the case where the eNBs are synchronised and the case where the eNBs are not synchronised. As shown, firstly for the case of the synchronised eNBs, the source eNB alternatively transmits the PDCCH and the PDSCH (physical downlink shared channel). In FIG. 5, the PDCCH is shown with the hatching whilst the PDSCH is shown in grey. The source eNB alternatively transmits the PDCCH and the PDSCH. However, gaps 400 are provided in the transmission. A gap is where the source eNB does not transmit the PDCCH and/or the PDSCH for the UE. For synchronised eNBs, the target eNB will transmit its PDCCH during these gaps. Thus, the user equipment will be able to monitor the PDCCH channel of the target eNB in these gaps. Further, the user equipment will know the possible transmission times of the PDCCH targeted for that user equipment and will monitor those possible transmission times.

FIG. 5 also shows a scenario where the eNBs are not synchronised eNBs. As can be seen, the source eNB alternatively transmits the PDCCH and the PDSCH without any gaps. The target eNB will transmit the PDCCH for the user equipment. Again, the user equipment will know the possible transmission times of the PDCCH targeted for that user equipment. The user equipment will stop monitoring the source eNB PDCCH and/or PDSCH when it expects the PDCCH from the target eNB. Thus, the user equipment will skip reception of some sub-frames when receiving the PDCCH from the target eNB. In some embodiments, this may mean that the user equipment does not need to have a dual receiver.

It should be appreciated that in some embodiments, the user equipment may have a dual receiver and be able to monitor both the source eNB PDCCH and the target eNB PDSCH.

It should be appreciated that the channels shown in FIG. 5 are from the perspective of the user equipment.

In some embodiments, the user equipment will know when to expect the PDCCH from the target eNB. In one embodiment, the timing of the PDCCH is based on the user equipment ID and/or cell ID. Thus, both the target eNB and the user equipment will be able to determine the timing of the relevant PDCCH.

In the case of synchronised eNBs, the source eNB will have interruptions in the transmission of the PDCCH and PDSCH to allow the user equipment to measure the target eNBs. In the case of non-synchronised eNBs, the user equipment will skip reception of the PDCCH from the source eNB to allow the user equipment to receive the PDCCH.

Figure 6:
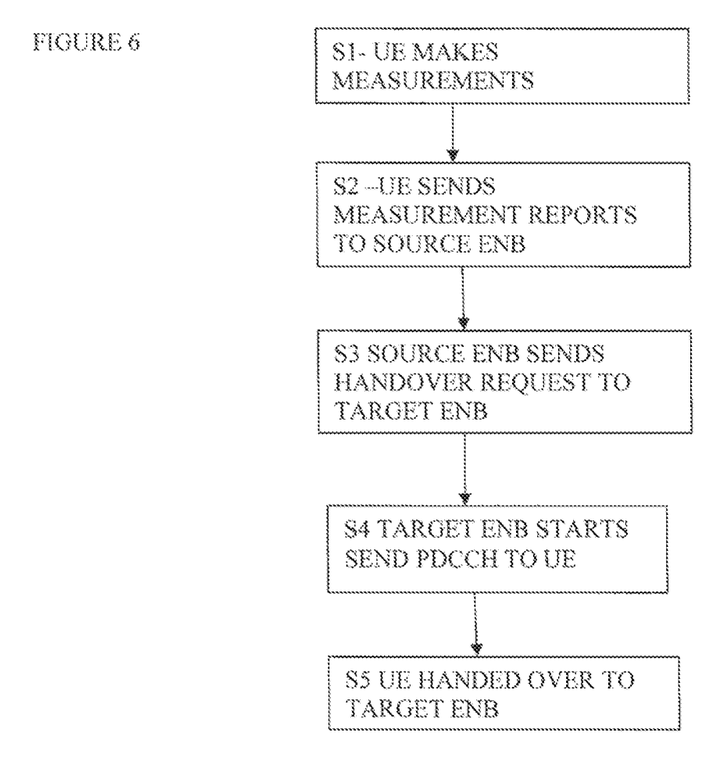
FIG. 6 shows a method of an embodiment.

Reference is now made to FIG. 6 which shows a method. In step S1, the UE makes measurements, as discussed above.

In step S2, the UE sends the measurement reports to the source eNB. As mentioned previously, one or other or both of the UE and source eNB will decide that handover to the target eNB is required. The UE may start monitoring the PDDCH even before the measurement report is sent, as the measurement report is sent or after the measurement report is sent. Of course instead of the measurement report, information indicative of a need for handover may be sent. However, until the target eNB has received the handover request for the PDDCH or made a determination that handover of the UE to that target eNB is possible or likely, the PDDCH will not have any information for the UE.

In step S3, the source eNB send a handover request to the target eNB via the X2 connection or the like.

In step S4, the target eNB starts to send the PDDCH to the UE, as discussed previously.

In step S5, the UE is handed over the target eNB.

Some embodiments may have an advantage in that the PDCCH decoding efforts are reduced because the user equipment will know when to expect the PDCCH from the target eNB.

In some embodiments, the eNodeBs are synchronised in TD (time division)-LTE. In FDD (frequency division duplex)-LTE, the eNBs may not be synchronised. The synchronised embodiment of FIG. 4 may be appropriate in the case of TD-LTE and the non synchronised embodiment of FIG. 5 may be appropriated in the case of FDD-LTE.

Thus in some embodiments, the UE should find out the timing of the target cell as part of the neighbour cell measurements. In some embodiments, the cell ID+UE ID combination then defines the timing of PDCCH relative to the common channel timing of the target cell. In some embodiments, there may be a pre-defined mapping from Cell IE and/or UE ID to the transmission timing.

In some embodiments, the target cell may start providing the PDDCH for the UE, even where the UE has not sent a measurement report to the source eNB.

In some embodiments the target eNB is configured to provide the PDCCH at a time expected by the UE. There may be some limitations for the configurations for the control channel to be used and/or on the limitation of the time(s) when such a control channel may occur.

Reference has been made to the PDDCH and PDSCH channels. It should be appreciated that other embodiments may use only one of these channels. Other embodiments may use one or more different channels.

It is noted that whilst embodiments have been described in relation to LTE-Advanced, similar principles can be applied to any other communication system or indeed to further developments with LTE. Also, instead of carriers provided by a base station a carrier comprising may be provided by a communication device such as a mobile user equipment. For example, this may be the case in application where no fixed equipment provided but a communication system is provided by means of a plurality of user equipment, for example in adhoc networks. Therefore, although certain embodiments were described above by way of example with reference to certain exemplifying architectures for wireless networks, technologies and standards, embodiments may be applied to any other suitable forms of communication systems than those illustrated and described herein. In some other embodiments the aforementioned embodiments can be adopted to orthogonal frequency division multiple access (OFDMA) frequency division duplex (FDD) based mobile communication system other than LTE.

The required data processing apparatus and functions of a base station apparatus, a communication device and any other appropriate apparatus may be provided by means of one or more data processors. The described functions at each end may be provided by separate processors or by an integrated processor. The data processors may be of any type suitable to the local technical environment, and may include one or more of general purpose computers, special purpose computers, microprocessors, digital signal processors (DSPs), application specific integrated circuits (ASIC), gate level circuits and processors based on multi core processor architecture, as non limiting examples. The data processing may be distributed across several data processing modules. A data processor may be provided by means of, for example, at least one chip. Appropriate memory capacity can also be provided in the relevant devices. The memory or memories may be of any type suitable to the local technical environment and may be implemented using any suitable data storage technology, such as semiconductor based memory devices, magnetic memory devices and systems, optical memory devices and systems, fixed memory and removable memory.

In general, the various embodiments may be implemented in hardware or special purpose circuits, software, logic or any combination thereof. Some aspects of the invention may be implemented in hardware, while other aspects may be implemented in firmware or software which may be executed by a controller, microprocessor or other computing device, although the invention is not limited thereto. While various aspects of the invention may be illustrated and described as block diagrams, flow charts, or using some other pictorial representation, it is well understood that these blocks, apparatus, systems, techniques or methods described herein may be implemented in, as non-limiting examples, hardware, software, firmware, special purpose circuits or logic, general purpose hardware or controller or other computing devices, or some combination thereof.

The embodiments of this invention may be implemented by computer software executable by a data processor of the communication device, base station and/or control apparatus such as in the processor entity, or by hardware, or by a combination of software and hardware.

Further in this regard it should be noted that any blocks of the logic flow as in the Figures may represent program steps, or interconnected logic circuits, blocks and functions, or a combination of program steps and logic circuits, blocks and functions. The software may be stored on such physical media as memory chips, or memory blocks implemented within the processor, magnetic media such as hard disk or floppy disks, and optical media such as for example DVD and the data variants thereof, CD.

The foregoing description has provided by way of exemplary and non-limiting examples a full and informative description of the exemplary embodiment of this invention.

However, various modifications and adaptations may become apparent to those skilled in the relevant arts in view of the foregoing description, when read in conjunction with the accompanying drawings and the appended claims. However, all such and similar modifications of the teachings of this invention will still fall within the scope of this invention as defined in the appended claims. Indeed there is a further embodiment comprising a combination of one or more of any of the other embodiments previously discussed.

The invention claimed is:

1. A method comprising:
monitoring a control channel transmitted by a source base station;
providing information indicating that a user equipment is to be handed over to a target base station; and
monitoring a control channel transmitted by said target base station, while skipping reception of the control channel transmitted by the source base station, at time periods determined in dependence on identity information associated with said user equipment.

2. A method as claimed in claim 1, wherein said identity information comprises at least one of user equipment identity and cell identity.

3. A method as claimed in claim 1, wherein said control channel transmitted by said target base station comprises a physical downlink control channel.

4. An apparatus comprising at least one processor and at least one non-transitory computer readable medium including computer program code, the at least one non-transitory computer readable medium and computer program code configured, with the at least one processor, to cause the apparatus to:
monitor a control channel transmitted by a source base station;
provide information indicating that a user equipment is to be handed over to a target base station; and
monitor a control channel transmitted by said target base station, while skipping reception of the control channel transmitted by the source base station, at time periods determined in dependence on identity information associated with said user equipment.

5. An apparatus as claimed as in claim 4, wherein said identity information comprises at least one of user equipment identity and cell identity.

6. An apparatus as claimed in claim 4, wherein said control channel transmitted by said target base station comprises a physical downlink control channel.

* * * * *